United States Patent [19]

Bower

[11] Patent Number: 5,615,413
[45] Date of Patent: Apr. 1, 1997

[54] EYE SHIELD FOR VISOR OR CAP BILL

[76] Inventor: Kirk Bower, 2817 Rawhide Dr., Rapid City, S. Dak. 57702

[21] Appl. No.: 618,643

[22] Filed: Mar. 19, 1996

[51] Int. Cl.⁶ .................. A42B 1/24; A61F 9/00
[52] U.S. Cl. .................. 2/10; 2/209.13; 351/155
[58] Field of Search .................. 2/10, 453, 6.5, 2/6.7, 12, 13, 175.1, 195.1, 209.13; 351/155, 158

[56] References Cited

U.S. PATENT DOCUMENTS

| | | | |
|---|---|---|---|
| 1,665,513 | 4/1928 | Thomas | 2/10 |
| 1,696,198 | 12/1928 | Gross | 2/10 |
| 2,519,959 | 8/1950 | Fisher | 2/10 |
| 2,549,445 | 4/1951 | Friess | 2/10 |
| 2,648,091 | 8/1953 | Jones | 2/10 |
| 2,654,089 | 10/1953 | Tannenbaum | 2/10 |
| 2,677,129 | 5/1954 | Bigler | 2/10 |
| 4,210,972 | 7/1980 | Baclit | 2/10 |
| 4,541,125 | 9/1985 | Phillips | 2/10 |
| 4,819,274 | 4/1989 | Day | 2/10 |
| 5,007,109 | 4/1991 | Wheeler | 351/155 |
| 5,056,164 | 10/1991 | Lisle et al. | 2/453 |
| 5,129,102 | 7/1992 | Solo | 2/10 |
| 5,208,916 | 5/1993 | Kelman | 2/10 |
| 5,261,124 | 11/1993 | Day | 2/10 |
| 5,412,812 | 5/1995 | Gatchalian | 2/10 |
| 5,422,686 | 6/1995 | Kelman et al. | 2/10 |
| 5,533,207 | 7/1996 | Diaz | 2/453 |

FOREIGN PATENT DOCUMENTS

| | | | |
|---|---|---|---|
| 135356 | 4/1952 | U.S.S.R. | 2/10 |
| 269968 | 4/1927 | United Kingdom | 2/10 |
| 996545 | 6/1965 | United Kingdom | 2/10 |

*Primary Examiner*—Amy B. Vanatta
*Attorney, Agent, or Firm*—Gene R. Woodle

[57] ABSTRACT

Embodiments of an eye shield for a visor or cap bill which may be removably attached to the bill of a visor or cap by pressing clips onto the right edge and the left edge of the bill of a visor or cap. Anchors are provided which may be removably attached to the clips by hinge pins which protrude downward through the clips. The anchors are attached to an eye shield and the eye shield may be flipped down to protect the user's eyes from various environmental irritants or flipped upward inconspicuously out of the user's line of vision.

4 Claims, 2 Drawing Sheets

EYE SHIELD FOR VISOR OR CAP BILL

BACKGROUND OF THE INVENTION

1. Field of the Invention

The present invention relates generally to detachable eye shields for visor or cap bills and more particularly to such an eye shield which may be flipped down to an in use position or flipped up parallel to the bill when not in use.

2. Background Information

The invention presented in the present application is believed to solve, in a simple and effective fashion, a problem which has long plagued persons engaged in activities in which various environmental factors adversely affect the eyes a method of protecting the eyes from such environmental factors which is convenient, effective, and efficient. For example, many persons engaged in activities such as baseball, skiing, boating, and construction have a need to protect their eyes from the sun or wind. Such persons commonly wear sun glasses or goggles for eye protection and comfort, but often find it inconvenient to carry these items or to store them when not in use. These person also commonly wear a visor or cap which includes a bill which protrudes forward from the cap or visor.

Several attempts have been made to at least partially solve problems relating eye protection for persons wearing visors or caps.

One such attempt is disclosed in the patent to Gatchalian (U.S. Pat. No. 5,412,812, May 9, 1995). This patent discloses a detachable eye shield attachment for visor caps or the like. The device includes a centrally hinged shield attached to a mounting base with a screw which protrudes upward through a hole in the bill of the hat. The mounting base is held in place by a wing nut which is screwed onto the screw from the top of the bill. The shield may be positioned either downward perpendicular to the bill or upward parallel to the bill.

Another attempt to solve problems relating to eye protection for persons wearing visors or caps is disclosed in the patent to Solo (U.S. Pat. No. 5,129,102, Jul. 14, 1992). This patent discloses a cap provided with removable flip up and down glasses. The shield is very similar to that disclosed in Gatchalian with a central hinge. The method of attachment is two hook-and-loop strips. One of the strips is affixed to the underside of the cap bill and the other is affixed to the top of the hinge structure. The strips are complementary and allow the shield and hinge assembly to be removably attached to the underside of the bill.

The ideal eye shield for a visor or cap bill provides an eye shield which may be positioned either in an in use or vertical position or in a nearly horizontal position away from the line of the user's sight when not in use The ideal eye shield for a visor or cap bill would also be usable on a wide variety of conventional visors or caps without modification of the eye shield or modification of the visor or cap The ideal eye shield for a visor or cap bill would be stable and not subject to movement or vibration when in use. The ideal eye shield for a visor or cap bill should also be simple, lightweight, compact, unobtrusive, easy to use, and inexpensive.

SUMMARY OF THE INVENTION

The present invention provides an eye shield for a visor or cap bill which includes an eye shield which may be flipped down when in use or flipped up and out of the way when not in use. The invention includes two "C" shaped clips which may be pressed onto the sides of the bill of a conventional visor or cap A hinge pin with a head is placed downward through holes in each of the clips. The hinge pins are bent at a right angle just below the bottom surface of each clip. The shield has two anchors, one affixed to either side of the top of the shield. The anchors each include a hole parallel to the top of the shield along the longitudinal axis of each anchor. The shield and anchors are removably attached to the clips by inserting the lower portion of each anchor pin into the holes in the anchors. The pins act as hinges so that the shield may be placed in an in use, vertical position or placed parallel to the bill when the shield is not in use. There are two spurs on the underside of each clip which are positioned such that they press against the anchors to hold the shield in either the up position or the down position. Because shield attachment is a simple matter of inserting the anchor pins into holes in the anchors, a variety of shields having different properties could be used without the necessity of changing clips or anchor pins.

One of the major objects of the present invention is to provide an eye shield for a visor or cap bill which provides an eye shield which may be positioned either in an in use or vertical position or in a horizontal position away from the line of the user's sight when not in use.

Another objective of the present invention is to provide an eye shield for a visor or cap bill usable on a wide variety of conventional visors or caps without modification of the eye shield or modification of the visor or cap.

Another objective of the present invention is to provide an eye shield for a visor or cap bill which is stable and not subject to movement or vibration when in use.

Another objective of the present invention is to provide an eye shield for a visor or cap bill which is simple, lightweight, compact, unobtrusive, easy to use, and inexpensive.

Another objective of the present invention is to provide an eye shield for a visor or cap bill with which a variety of shields having different properties may be used.

These and other features of the invention will become apparent when taken in consideration with the following detailed description and the drawings.

DESCRIPTION OF THE PREFERRED EMBODIMENT

Figure 1:
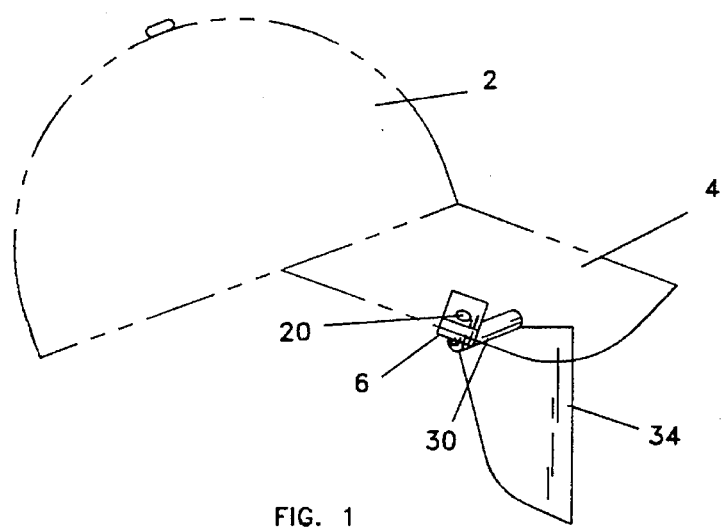
FIG. 1 is a side view of a preferred form of an eye shield for visor or cap bill of the present invention in the down position.

Referring to the drawings, FIGS. 1 through 8, there is shown a preferred form of the eye shield for visor or cap bill embodying the present invention.

Referring to FIG. 1, a cap 2 represents any of a wide variety of visors or caps having a bill 4 which protrudes forward from the front edge of the cap 2.

Figure 6:
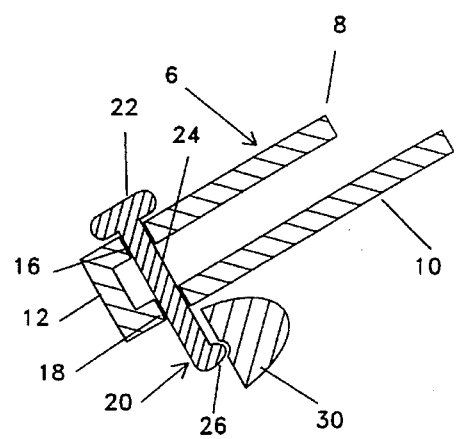
FIG. 6 is a sectional view of the eye shield for visor or cap bill taken along line 6—6 of FIG. 5.

Referring now to FIG. 6, there are two identical clips 6 which include an upper leg 8 and a lower leg 10 which are parallel. The upper leg 8 and the lower leg 10 are joined by a connecting leg 12 which is perpendicular to said upper leg 8 and said lower leg 10 such that the distance between the closest faces of said upper leg 8 and said lower leg 10 is the same as the thickness of the bill of a conventional visor or cap. Said upper leg 8 is slightly shorter than said lower leg 10.

Figure 3:
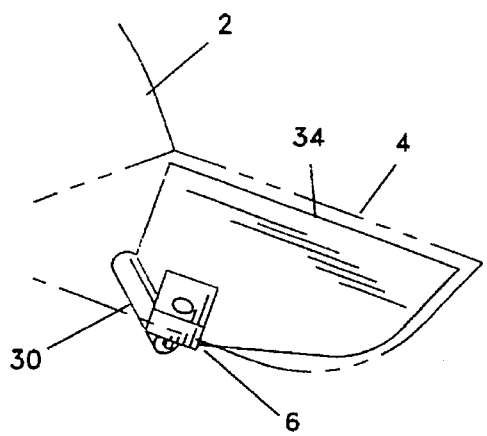
FIG. 3 is a side view of the eye shield for visor or cap bill in the up position.

Referring now to FIG. 3, the two clips 6 may be pressed onto either side of the bill 4 such that said upper legs 8 and said lower legs 10 are parallel to said bill 4.

Figure 7:
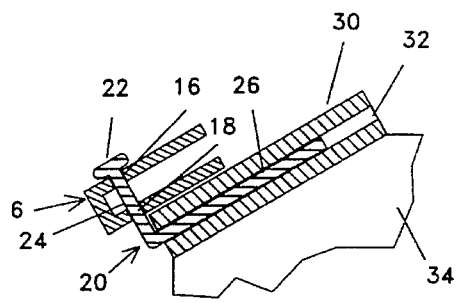
FIG. 7 is a sectional view of the eye shield for visor or cap bill taken along line 7—7 of FIG. 5.

Referring now to FIG. 7, there is a hole 16 through and perpendicular to each of said legs 8 through the edge of said upper legs 8 nearest the connecting leg 12. There is a hole 18 through and perpendicular to each of said lower legs 10 through the edge of said lower legs 10 nearest the connecting leg 12. The holes 16 and the holes 18 are aligned and, when said clips 6 are attached to said bill 4, are between the outer edge of said bill 4 and said connecting legs 12. There are two hinge pins 20 each of which is pushed downward through said holes 16 and said holes 18 in each of said clips 6. There is a head 22 on the top of each of the hinge pins 20 having a diameter slightly larger than the diameter of said holes 16 and said holes 18 which prevents said hinge pins 20 from moving downward through said holes 16 and said holes 18. The portions of said hinge pins 20 below the lowest face of said lower legs 10 are bent at right angles so that the upper portion of said hinge pins 20 is perpendicular to the top face of said upper leg 8 and the lower portion of said hinge pins 20 is parallel to the top face of said upper leg 8. The upper, roughly vertical, portion of each of said hinge pins 20 is upper hinge pin 24. The lower, roughly horizontal, portion of each of said hinge pins 20 is lower hinge pin 26. The lower hinge pins 26 protrude inward, generally toward the center of said bill 4.

Referring again to FIG. 7, two anchors 30 are provided. Each of the anchors 30 include an anchor hole 32 in the center of said anchors 30 and parallel to the longitudinal axis of said anchors 30. The diameter of the anchor holes 32 is slightly greater than the diameter of said hinge pins 20. Said lower hinge pins 20 may be inserted into each of said anchor holes 32. There is an eye shield 34 attached to said anchors 30. The eye shield 34 is the same length as the width of said bill 4 of said cap 2 if the width of said bill 4 were measured when said bill 4 were flat rather than curved. Said eye shield 34 is attached to said anchors 30 such that said anchors 30 are attached to the top of said eye shield 34 and the outermost edge of an anchor 30 is flush with each of the outermost edges of said eye shield 34.

Figure 4:
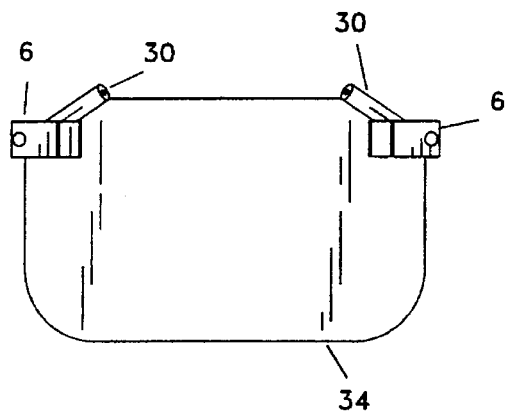
FIG. 4 is a front view of the eye shield for visor or cap bill in the down position.

Referring now to FIG. 4, the top, outside corners of said shield 34 are cut at an angle of approximately 40 degrees at the point where said shield 34 is attached to each of said anchors 30.

Referring now to FIG. 1 and FIG. 3, said lower hinge pins 26 inside said anchor holes 32 act as hinges such that said eye shield 34 may either be in the in use or vertical position shown in FIG. 1 or rotated forward and upward to the up position indicated by FIG. 3. With said eye shield in the in use or vertical position, the user's eyes are protected from various environmental elements. With said eye shield 34 in the up position, said eye shield 34 is out of the user's line of vision and rests inconspicuously against the bottom of said bill 4.

Figure 2:
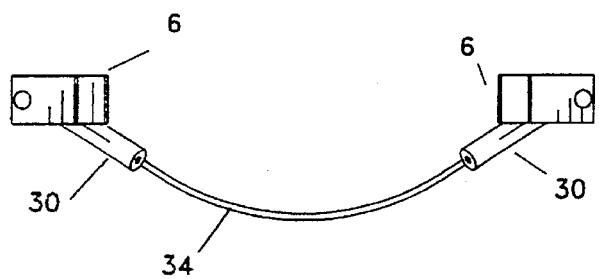
FIG. 2 is a top view of the eye shield for visor or cap bill in the down position.

Referring now to FIG. 2, the length of said shield 34 is such that, when said anchors 30 are in place, said shield 34 bows slightly forward at the center of said shield 34 with the bow toward the forward end of said bill 2.

Figure 5:
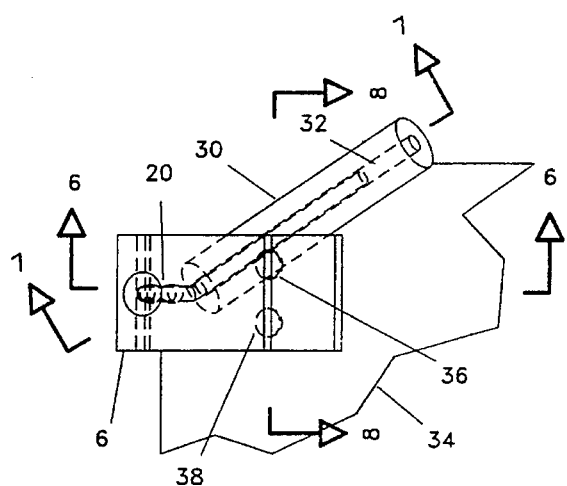
FIG. 5 is an enlarged top view of a portion of the eye shield for visor or cap bill in the up position.

Referring now to FIG. 5, there is an inner spur 36 having a generally hemispherical shape protruding downward form each of said clips 6. There is an outer spur 38 having a generally hemispherical shape also protruding downward form each of said clips 6. The inner spurs 36 and the outer spurs 38 are equidistant from the outer edge of said clips 6 with said inner spurs 36 rearward of said outer spurs 38.

Figure 8:
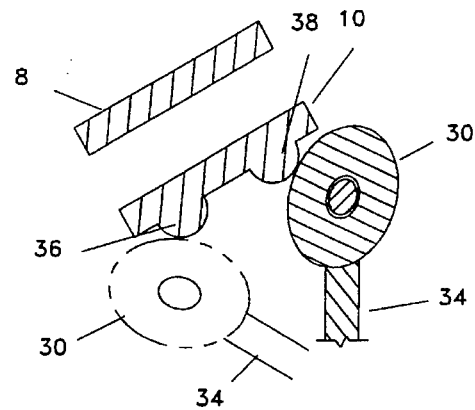
FIG. 8 is a sectional view of the eye shield for visor or cap bill taken along line 8—8 of FIG. 5.

Referring now to FIG. 8, solid lines show said anchor 30 and said shield 34 in the down or in use position. The phantom lines show said anchor 30 and said shield 34 in the up position. Said outer spur 38 is positioned such that, when said shield 34 is in the down position, the forward face of said outer spur 38 presses against the rearward face of said anchor 30 and holds said shield 34 in position. With said shield 34 in the up position the rearward face of said inner spur 36 presses against the forward face of said anchor 30, holding said shield 34 in the up position.

In operation the eye shield for visor or cap bill may be removably attached to a wide variety of visors or caps represented by said cap 2 by pressing said clips 6 onto the bill represented by said bill 4 of the visor or cap with one of said clips 6 on either side of the bill. When in use said eye shield 34 may be flipped down so that it is in the in use or vertical position. Said outer spurs 38 press against said anchors 30 and serve to hold said eye shield in position. When not in use said eye shield 34 may be flipped up, out of the user's line of sight, and said eye shield 34 rests unobtrusively against the underside of the bill. In the up position said inner spurs 36 press against said anchors 30 and serve to hold said eye shield 34 in the up position. If desired, a variety of said eye shields 34 could be provided having a variety of properties such as different tints, In the preferred embodiment of the eye shield for visor or cap bill said clips 6 and said anchors 30 are made from a tough, stiff plastic; but other materials such as spring steel or the like could be used. Said hinge pins 20 are made from steel in the preferred embodiments, but other materials having sufficient strength and stiffness could be used. Said eye shield 34 is made from tough plastic which is sufficiently flexible to be bent slightly to allow said lower hinge pins 26 to be inserted into said anchor holes 32 in said anchors 30. Said eye shield 34 must also be sufficiently strong and stiff to remain in position after attachment and should also be shatter resistant to prevent possible injury.

While preferred embodiments of this invention have been shown and described above, it will be apparent to those skilled in the art that various modifications may be made in these embodiments without departing from the spirit of the present invention. For that reason, the scope of the invention is set forth in the following claims:

I claim:

1. A detachable eye shield for visor or cap, the visor or cap having a bill which protrudes forward from the head covering portion of said visor or cap, and the bill having an upper surface, a lower surface, a forward edge away from the head covering portion of said visor or cap, a right edge on the user's right, and a left edge on the user's left, comprising:

(1) two clips which may be removably attached to said bill, one of the clips being attached to the right edge of said bill and one of the clips being attached to the left edge of said bill; said clips each having a hole perpendicular to the upper surface of said bill, the hole in said clip on the right edge of said bill being to the right of the right edge of said bill and the hole in said clip on the left edge of said bill being to the left of the left edge of said bill;

(2) two hinge pins inserted from the top down through said holes in each of said clips; the hinge pins each having a head at the top to prevent said hinge pins from moving completely through said holes; the bottom portions of said hinge pins being bent at a right angle from the top portions of said hinge pins;

(3) two anchors having holes through the center of their longitudinal axes; the anchors being adapted so that the bottom portions of said hinge pins may be inserted into the holes in said anchors thereby removably attaching one of said anchors to each of said hinge pins; and (4) an eye shield affixed to said anchors such that said anchor near the right edge of said bill is attached to the right side of the top of the eye shield and said anchor near the left edge of said bill is attached to the left side of the top of said eye shield;

whereby the eye shield for visor or cap bill may be removably attached to the bill of a visor or cap by pressing said clips onto the right edge and the left edge of said bill; said anchors and said eye shield may be removably attached to said clips by said hinge pins and said eye shield may be flipped down to serve as eye protection from various environmental irritants or flipped up inconspicuously out of the user's line of vision.

2. An eye shield for visor or cap bill of claim 1 in which locking means are provided for holding said eye shield in either a nearly vertical position below the lower surface of said bill or in a position parallel to and in proximity to the lower surface of said bill.

3. A detachable eye shield for visor or cap, the visor or cap having a bill which protrudes forward from the head covering portion of said visor or cap, and the bill having an upper surface, a lower surface, a forward edge away from the head covering portion of said visor or cap, a right edge on the user's right, and a left edge on the user's left and said bill having two holes, one near the right edge of said bill and one near the left edge of said bill, the two holes also being near the midpoint between the forward edge of said bill and the head covering portion of said visor or cap, comprising:

(1) two pins having the general shape of an "L", each of the pins having a shorter leg of the "L" which is slightly longer than the thickness of said bill and a longer leg of the "L" said pins each having a head being slightly larger than the holes in said bill on the end of the shorter leg away from the longer leg; said pins being adapted so that the longer legs of each pin may be inserted into one of said holes in said bill from the top of said bill and the heads will prevent said pins from moving completely through said holes and said longer legs will be parallel to the underside of said bill; and (2) an eye shield having anchors attached to the top of the eye shield at the outside edges of said eye shield; the anchors each having a hole through the center of its longitudinal axis, and said eye shield being adapted so that said longer leg of each of said pins may be inserted into the hole in each of said anchors;

whereby said pins may be inserted into said holes in said bill such that said pins are prevented from moving completely through said holes in said bill by the heads on said pins; said eye shield may be removably attached to said pins by inserting said pins on said eye shield into said holes in said anchors on said eye shield; and said eye shield may be flipped down to serve as eye protection from various environmental irritants or flipped up inconspicuously out of the user's line of vision.

4. An eye shield for visor or cap bill of claim 3 in which locking means are provided for holding said eye shield in either a nearly vertical position below the lower surface of said bill or in a position parallel to and in proximity to the lower surface of said bill.

* * * * *